United States Patent [19]

Pelletier et al.

[11] Patent Number: 5,164,160
[45] Date of Patent: Nov. 17, 1992

[54] INSTALLATION TO CARRY OUT CONTINUOUS MEASUREMENTS IN REAL TIME OF MASSES OF METALS IN AN ACID SOLUTION AND TO MEASURE THE ACIDITY OF THIS SOLUTION

[75] Inventors: Thierry Pelletier, Talant; Jacques Gontier, Asnieres-lès-Dijon, both of France

[73] Assignee: Commissariat a l'Energie Atomique, Paris, France

[21] Appl. No.: 509,771

[22] Filed: Apr. 17, 1990

[30] Foreign Application Priority Data

Apr. 18, 1989 [FR] France .................. 89 05126

[51] Int. Cl.$^5$ .................. G01N 21/05; G01N 33/20
[52] U.S. Cl. .................. 422/82.09; 422/53;
422/62; 422/68.1; 422/81; 422/82.05;
422/82.03; 422/159; 356/432; 356/436;
356/440; 356/246; 250/428; 250/432 R;
250/435; 252/627
[58] Field of Search .................. 422/53, 62, 68.1, 81,
422/82.03, 82.05, 82.09, 159; 356/432, 436, 440,
246; 250/428, 432 R, 435; 252/627

[56] References Cited

U.S. PATENT DOCUMENTS

| | | | |
|---|---|---|---|
| 2,998,520 | 8/1961 | Lanford et al. | 250/435 X |
| 3,531,644 | 9/1970 | Koster | 250/428 X |
| 3,791,221 | 2/1974 | Kirschner et al. | 422/82.09 X |
| 3,844,719 | 10/1974 | Hammitt | 422/82.09 |
| 3,898,042 | 8/1975 | Webb et al. | 422/62 X |
| 3,943,363 | 3/1976 | Amblard | 250/288 |
| 4,766,550 | 8/1988 | Byers et al. | 422/62 X |
| 4,844,887 | 7/1989 | Galle et al. | 422/82.03 X |
| 4,908,676 | 3/1990 | Bedell et al. | 356/440 X |
| 4,910,151 | 3/1990 | Platt | 422/81 X |
| 4,920,056 | 4/1990 | Dasgupta | 422/81 X |

OTHER PUBLICATIONS

Patent Abstracts of Japan, vol. 100, No. 12, p. 683, Apr. 2, 1988.

*Primary Examiner*—Robert J. Warden
*Assistant Examiner*—Stephanie Blythe
*Attorney, Agent, or Firm*—Finnegan, Henderson, Farabow, Garrett, Dunner

[57] ABSTRACT

The invention concerns an installation for carrying out continuous measurements in real time of masses of metals in an acid solution and measuring the acidity of this solution.

This installation comprises a pipe (1) for circulating this solution, means (2) traversed by the solution to measure the acidity of the latter and providing a signal representative of the value of this acidity, a flowmeter (4) connected to the pipe (1) and traversed by the solution and providing a signal representative of the value of the flowrate of this solution, a spectrometer (7) acting on the circulation cell (6) and providing a signal representative of the intensity of energy peaks respectively corresponding to the values of the concentrations of the metals in the solution, and a computer (9) connected to the means to measure acidity, to the spectrometer and to the flowmeter; this computer is also connected to a memory (9) in which a calculation program is recorded to calculate the respective masses of said metals from the values of the respective concentrations and values of the acidity and flowrate.

11 Claims, 3 Drawing Sheets

INSTALLATION TO CARRY OUT CONTINUOUS MEASUREMENTS IN REAL TIME OF MASSES OF METALS IN AN ACID SOLUTION AND TO MEASURE THE ACIDITY OF THIS SOLUTION

FIELD OF THE INVENTION

The present invention concerns an installation to carry out continuous measurements in real time of masses of metals in an acid solution and to measure the acidity of this solution. It applies more particularly to the continuous measurements in real time of masses of metals in a nitric acid solution, said masses of metals in particular being masses of plutonium, uranium and americium originating from a nuclear waste reprocessing plant and contained in this nitric acid solution.

BACKGROUND OF THE INVENTION

Currently, there is no installation making it possible to continuously measure in real time metal masses in an acid solution and in particular to measure masses of uranium, plutonium and americium contained in a nitric acid solution originating from a nuclear waste reprocessing plant.

The only known method to carry out such measurements of masses does not make it possible to obtain continuous results in real time. It does not use an autonomous unit able to be qualified as a "measurement installation". In fact, according to this known method, a small sample is taken from the acid solution containing metal masses and quantitative analyses are carried out making it possible to determine the values of these metal masses in the solution.

This method has a large number of drawbacks: the measurements of the masses effected by quantitative analysis are carried out from samples of the solution and not from the entire solution. These measurements are thus not made continuously in real time, take a long time to carry out (several hours) and are only valid for a small sample of the solution. Moreover and especially for the measurements of masses of uranium, plutonium and americium in a nitric acid solution, these quantitative analysis operations need to be carried out manually inside a glove box, these manual operations proving to be sometimes dangerous.

SUMMARY OF THE INVENTION

The object of the present invention is to overcome these drawbacks and in particular to embody an installation for carrying out measurements continously in real time, said invention concerning the entire solution and without the need for long dangerous handlings.

These objectives can be achieved by making the entire solution circulate in the installation and by carrying out measurements of the flowrate of the solution, acidity and the concentrations of the metals in this circulating solution.

The object of the invention is to provide an installation to continuously measure in real time masses of metals contained in an acid solution and the acidity of this solution, wherein it comprises a pipe for circulating this solution, means connected to the pipe and tranversed by the solution so as to measure the acidity of this solution, one output of these acidity measuring means providing a signal representative of the value of this acidity, a flowmeter connected to the pipe and traversed by the solution so as to provide on one output a signal representative of the value of the flowrate of this solution, a cell for circulating the solution and connected to the pipe and traversed by the solution, a spectrometer acting on the circulation cell so as to provide on one output a signal representative of the intensity of energy peaks respectively corresponding to the values of the concentrations of the metals in the solution, and a computer connected to the outputs of the acidity measuring means, the spectrometer and to the flowmeter, this computer also being connected to a memory in which a calculation program is recorded, said program calculating the respective masses of said metals from the values of said respective concentrations, and from the acidity values and from the flowrate.

According to another characteristic of the invention, said circulation cell comprises a pipe for admitting the solution, said pipe being connected to said circulation pipe and opening into a transit tank, and a pipe for expelling the solution contained in said transit tank to a storage receptacle, said spectrometer comprising a source for irradiating the solution, an energy peak detector having one outlet constituting said output of the spectrometer, and a sealed cylindrical well for irradiating said circulation cell at the time the measurements are made, said well being disposed vertically between the irradiation source and the detector so as to irradiate the solution in the transit tank, this irradiation well having a bottom and cylindrical lateral wall and, at one upper extremity, an opening for introducing said cell into said well.

According to another characteristic, said circulation cell is an impervious hollow cylinder containing said transit tank, this cylinder representing an upper base from which said solution admission and evacuation pipes come out, a lower base with said transit tank being situated close to the latter, and a cylindrical enclosure integral with said bases, the introduction of said circulation cell into said irradiation well making a volume appear between said cylindrical enclosure of the cell and the inside of said well, this volume being hermetically sealed at least close to the opening of said irradiation well by joints integral with said enclosure.

According to another characteristic, the circulation cell comprises a solution leak detection volume, said volume being situated inside said cylinder between the lower base of this cylinder and the transit tank, the installation further comprising means to detect any leak of the solution in the detection volume, these detection means being connected to an alarm.

According to another characteristic, the solution leak detection means comprise two electrodes situated in the detection volume, these electrodes being connected to alarm triggering means by connection means traversing the lower base of the circulation cell and the bottom of said irradiation well.

According to another characteristic, the circulation cell comprises above the transit tank inside said cylinder an expansion volume intended to contain the solution in the event of any leak occuring.

According to another characteristic, the circulation cell further comprises a circulation cell stand-by receptacle for the reserve transferring of the circulation when no measurement has been carried out, this receptacle having the shape of a sealed cylindrical support vessel having a bottom, a cylindrical lateral wall and an upper extremity having an opening for introducing the circulation cell, this introduction of the circulation cell into the support vessel making a volume appear between the cylindrical enclosure of the cell and the wall of the support vessel, this receptacle comprising means for detecting any leak of the solution in the volume between the enclosure of the cell and the wall of the support vessel, these means being connected to said alarm.

According to another characteristic, the flowmeter and the acidity measuring means are situated in a glove box, said pipe imperviously traversing this glove box, said solution admission and evacuation pipes traversing this glove box via a window having a circumference delimited by a frame, this frame being hermetically connected by a sealed flexible sleeve to the upper base of the circulation cell, said admission and evacuation pipes being situated in said sleeve, said evacuation pipe opening into a receptacle situated in the glove box, said stand-by receptacle being integral with the glove box.

According to another characteristic, the spectrometer, computer, alarm triggering means, the alarm and the irradiation well collectively form a unit able to be moved close to the various glove boxes, each glove box having its own flowmeter, acidity measuring means, circulation cell, stand-by receptacle and flexible sleeve.

According to another characteristic, the installation is designed to measure masses of plutonium, uranium and americium in a solution of nitric acid and to measure the acidity of this solution.

According to another characteristic, the acidity measuring means comprise an enclosure having a solution inlet and an outlet both connected to said circulation pipe so that this enclosure is traversed by the solution, a reference electrode and a measuring electrode being submerged in the solution inside said enclosure in a direction perpendicular to that of the solution circulation, these two electrodes being connected to a voltage measuring device having one output constituting said output which supplies a signal representative of the acidity of the solution.

BRIEF DESCRIPTION OF THE DRAWINGS

The characteristics and advantages of the invention shall appear more readily from a reading of the following description with reference to the accompanying drawings in which.

DETAILED DESCRIPTION OF THE PREFERRED EMBODIMENTS

Figure 1:
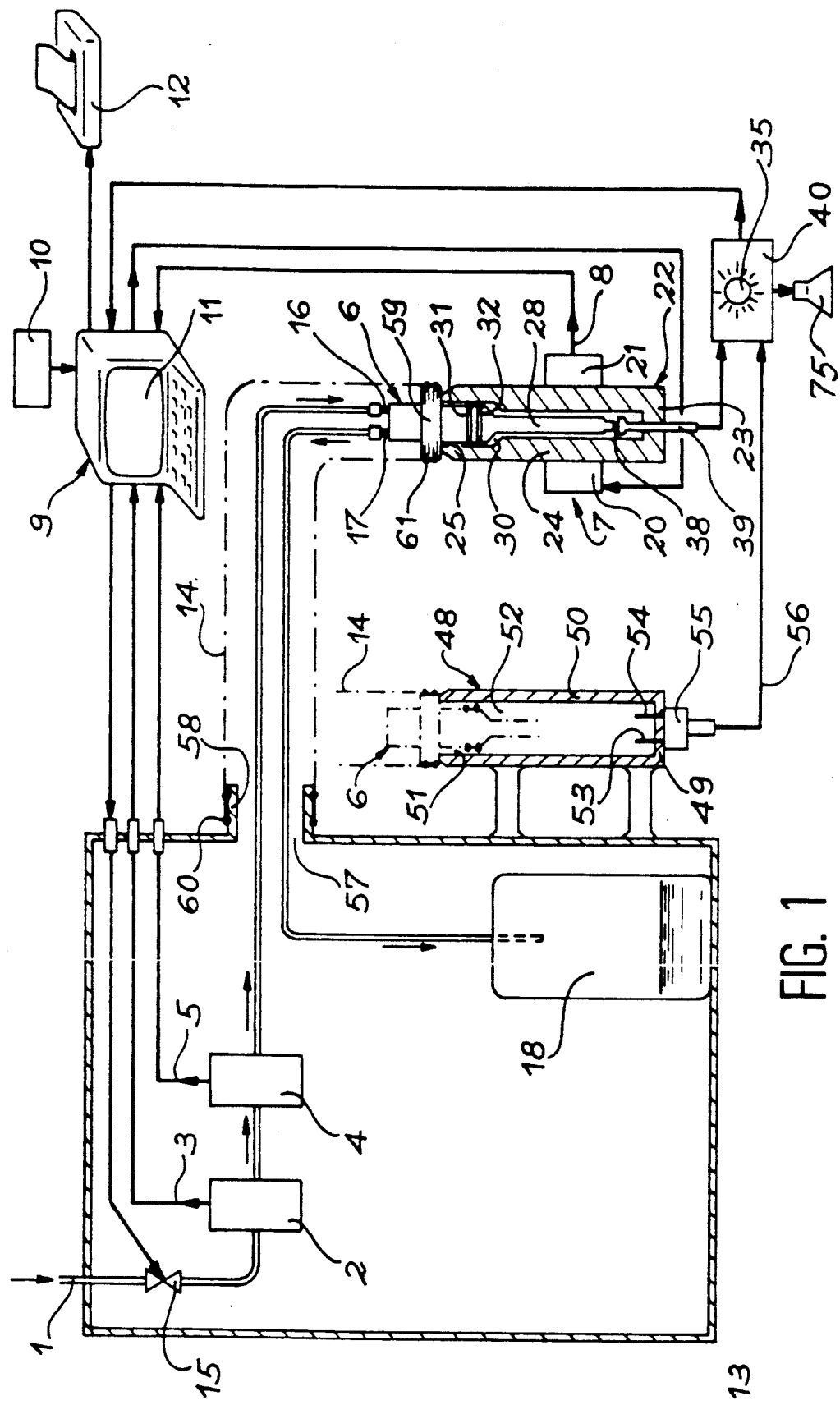
FIG. 1 diagrammatically represents a measuring installation according to the invention, FIG. 2 diagrammatically shows a longitudinal cutaway view of a solution circulation cell belonging to the installation of the invention, FIG. 3 diagrammatically shows a cutaway view of the solution acidity measuring means belonging to the installation of the invention, FIG. 4 diagrammatically shows a longitudinal cutaway view of a reference cell used in the installation of the invention.

The installation of the invention represented diagrammatically on FIG. 1 comprises a pipe 1 for circulating the acid solution containing the metal masses it is desired to determine. It also comprises means 2 connected to the pipe 1 and traversed by the solution so as to measure the acidity of the latter. One output 3 of these measuring means 2 supplies, as shall be seen later in detail, a signal representative of the value of this acidity. The solution circulating in the pipe 1 is derived from a storage chamber (not shown).

A flowmeter 4 is connected to the pipe 1 behind the acidity measuring means 2. This flowmeter is traversed by the solution and supplies on an output 5 a signal representative of the flowrate of this solution in the pipe 1. This flowmeter is, for example, an electromagnetic type flowmeter and shall not be further described in detail.

The installation also comprises a cell 6 for circulating the solution, this cell being connected to the pipe 1, for example behind the flowmeter 4. It is traversed by the solution and shall be later described in detail.

Finally, the installation comprises a spectrometer 7 acting on the circulation cell 6 and supplying on one output 8 a signal representative of the intensity of energy peaks respectively corresponding to the values of the concentrations of the various metals contained in the acid solution. A computer 9 is connected to the outputs 3, 5 and 8 of the acidity measuring means 2, the flowmeter 4 and the spectrometer 7. This computer is also connected to a memory 10 in which a calculation program is recorded, said program calculating the respective masses of the metals present in the acid solution; this calculation is made on the basis of the values of the respective concentrations of these metals and the acidity and flowrate values of the solution. This calculation shall be described later in detail. The computer may be provided with a display screen 11 and be connected to a printer 12 able to print the measuring results.

In a first embodiment in which the installation is used to measure masses of non-radioactive metals, no special protection device is actually used; in a second embodiment, the installation is used to measure masses of radioactive metals, such as plutonium, uranium and americium; the installation then comprises a glove box 13, as well as various protection elements, such as a sealed flexible sleeve 14, said elements to be described subsequently in detail.

FIG. 1 also shows an electrovalve 15 making it possible, as shall be seen subsequently, to control the circulation or stoppage of the circulation of the solution in the pipe 1.

The circulation cell 6 containing the solution comprises a pipe 16 admitting this solution and a pipe 17 for expelling the latter. The admission pipe 16 is connected to the circulation pipe 1, for example, behind a flowmeter 5. The evacuation pipe 17 may, for example, open into a solution recovery tank 18.

Figure 2:
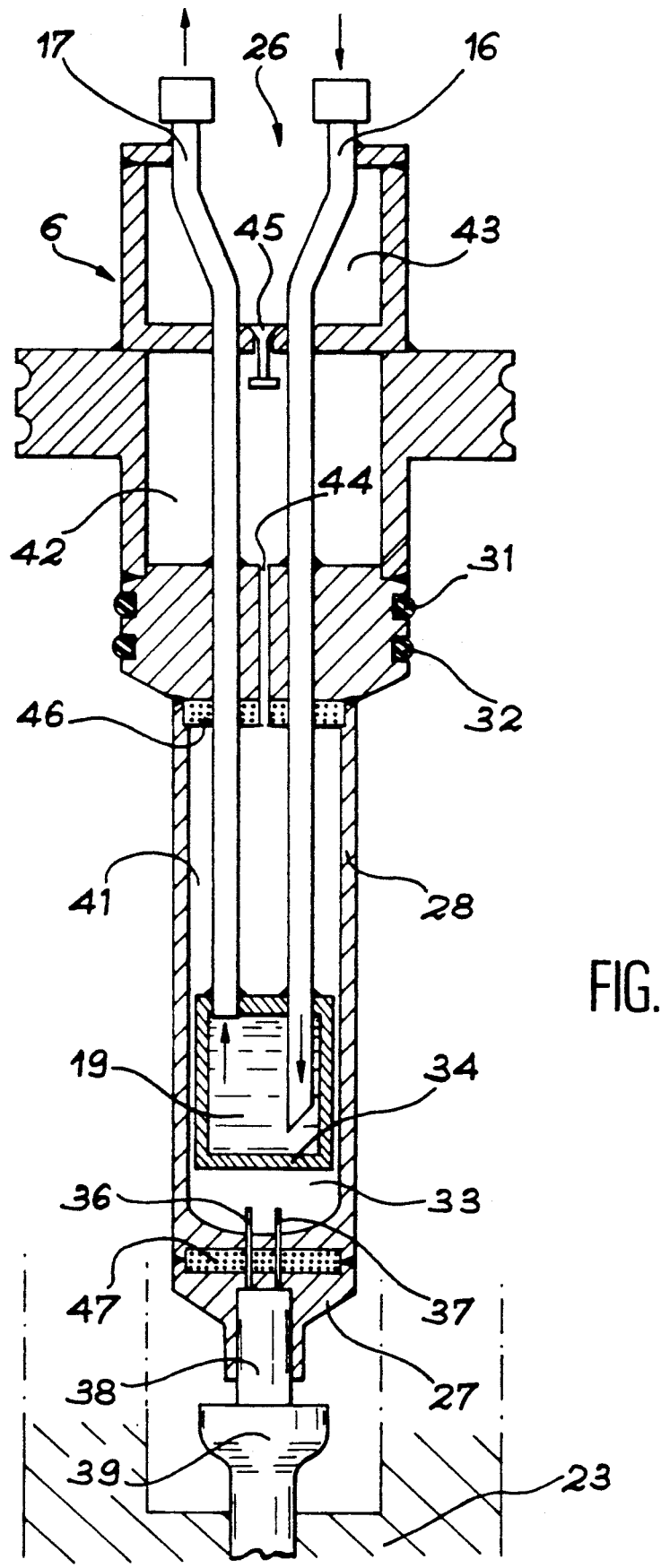

The structure of the solution circulation cell 6 shall be more readily understood from perusing FIG. 2 showing a longitudinal cutaway view of this cell. The pipe 16, which is connected to the circulation pipe 1, and the pipe 17, which is connected to the tube for expelling the solution into a receptacle 18, open into a transit tank 19. This figure shall later be described in more detail.

With reference again to FIG. 1, the spectrometer 7 comprises a source 20 for irradiating the solution and an energy peak detector 21 detecting any radiations derived from the irradiated solution; these radiations are, for example, X-rays and/or gamma rays. The source 20 and the detector are well-known in the prior art and are not here described in detail. The detector 21 has one output which constitutes the output 8 of the spectrometer; this output supplies the signal representative of the intensities of energy peaks respectively corresponding to the various metals contained in the solution. These intensities are proportional to the respective concentrations of the various metals contained in the solution.

The installation also comprises a sealed cylindrical well 22, the irradiation of the circulation cell 6 taking place during the course of measurements. This well is disposed vertically between the irradiation source 20 and the detector 21 so as to irradiate the solution in the transit tank 19 (FIG. 2). This cylindrical irradiation well is sealed; it comprises a bottom 23, a cylindrical lateral wall 24 and, at one upper extremity, an opening 25 for introducing the circulation cell 6 into this well.

As shown on FIG. 2, the circulation cell 6 is a sealed hollow cylinder containing the transit tank 19. This cylinder has an upper base 26 from which the solution admission and evacuation pipes 16 and 17 respectively come out, and a lower base 27 close to the transit tank 19 inside the cell. The upper and lower bases are brought together sealed by a cylindrical casing 28; this casing may moreover be constituted by several cylindrical casings with different diameters and joined together by welds (not shown on this figure).

With reference again to FIG. 1, it can be seen that the introduction of the circulation cell 6 into the irradiation well 22 makes a volume 30 appear between the casing 28 of the cell 6 and the inside of the wall 24 of the irradiation well 22. This volume is hermetically sealed, at least close to the opening 25 of the irradiation well 22. This hermetic sealing may be effected, for example, by means of O-rings 31, 32 being engaged in the throats of the cylindrical casing 28 of the cell so as to be rendered integral with the latter.

As shown in more detail on FIG. 2, the irradiation cell 6 also comprises a volume 33 making it possible to detect any possible leak of the solution normally contained in the tank 19. This leak may also originate from the admission and evacuation pipes 16 and 17. This volume is situated inside the hollow cylinder of the cell 6 between the lower base 27 of the cell 6 and the bottom 34 of the transit tank 19.

Means to detect any possible leak of the solution in the detection volume 33 are connected to a visual 35 and/or sound alarm 75. As shown on FIG. 2, they are constituted by two electrodes 36, 37 which, via non-conducting sealed passages, traverse the lower base 27 of the cell 6 and which open into the detection volume 33. Whenever a leak of the solution occurs in the volume 33, these two electrodes are short-circuited; they are connected to a male connector 38 which cooperates with a female connector 39 imperviously traversing the bottom 23 of the irradiation well 22. The leak detection means also comprise alarm triggering means 40 connected to the female connector 39. These alarm triggering means are not described here in detail. In particular, they include a d.c. supply source connected to the electrodes, means for amplifying a short-circuit signal between the electrodes, and means to shape this signal so as to trigger the alarm should any short-circuit occur between the electrodes.

The circulation cell 6 has, above the transit tank 19 inside the hollow cylinder constituting this cell, an expansion volume constituted in the embodiment represented on FIG. 2 by, for example, compartments 41, 42, and 43 placed in communication by a pipe 44 and by an opening provided with a valve 45. This expansion volume is designed to contain the solution should any leak occur from the tank 19 or from the pipes 16, 17 above this tank.

In the embodiment where the installation is used to carry out measurements of masses of plutonium, uranium and americium contained in solutions originating from nuclear waste reprocessing plants, lead protection disks 46, 47 are provided inside the hollow cylinder constituting the circulation cell 6, these disks being respectively situated at the upper and lower sections of this cell on both sides of the transit tank 19. They are not provided when the installation is used to carry out measurements concerning non-radioactive substances not emitting any dangerous radiations.

The installation further comprises, as shown on FIG. 1, a receptacle 48 for the reserve transferring of the circulation cell 6; this cell is placed in the receptacle when no measurement is made. This receptacle has the shape of a cylindrical sealed support vessel having a bottom 49 and a cylindrically-shaped lateral wall 50. This support vessel 48 has at one upper extremity an opening to introduce the circulation cell.

The introduction of the circulation cell 6 into the receptacle 48 makes a volume 52 appear between the cylindrical casing of the cell 6 and the lateral wall 50 of the support vessel. In the embodiment where the installation is used to carry out measurements concerning radioactive substances, the receptacle 48 comprises means to detect any possible leaking of the solution into the volume 52 between the casing of the cell 6 and the wall 48 of the support vessel; these detection means are connected to a visual 35 and/or sound 36 alarm. As previously, they are constituted by two electrodes 53, 54 connected to the alarm triggering means 40 by means of a connector 55 and a link 56. In the event of any leak of the solution in the volume 52, a short-circuit is established between the electrodes 53 and 54 and the alarm is triggered. The alarm triggering means 40 may also be connected to the computer 9 so as to record and display this alarm in the results supplied by the printer 12 and/or the screen 11. In the event of an alarm being triggered, the computer 9 halts the circulation of the solution by ordering the closing of the electrovalve 15.

In the embodiment when the installation is used for carrying out measurements concerning radioactive substances and as indicated earlier, said installation comprises a glove box 13, the pipe 1 imperviously traversing this sealed box, the electrovalve 15 contained in this glove box is controlled by the computer 9 at the time the measurements are to be made. The solution admission and evacuation pipes 16 and 17 traverse the glove box via a window 57 having a circumference delimited by a frame 58. This frame is hermetically connected by the sealed flexible sleeve 14 to one section 59 of the upper base 26 of the cell 6. Collars, such as 60, 61, make it possible to ensure the desired imperviousness. The solution admission and evacuation pipes 16 and 17 are situated in the sleeve 14, the pipe 17 opening, as indicated earlier, into the receptacle 18 situated in the glove box 13. In this embodiment, the receptacle 48 of the circulation cell is fixed to the glove box 13.

Figures 3, 4:
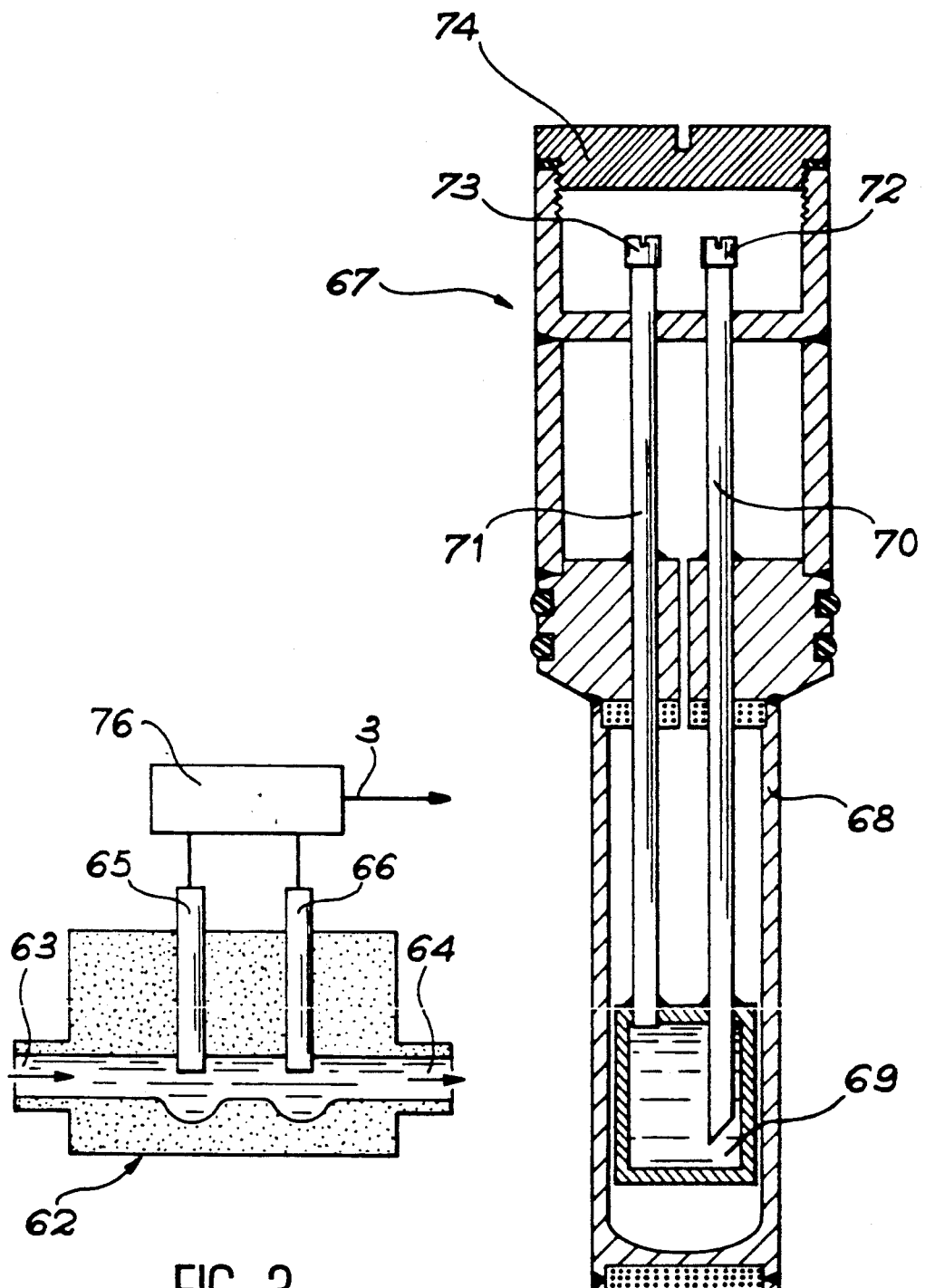

FIG. 3 shows a diagramatical longitudinal cutaway view of the means 2 to measure the acidity of the solution. These acidity measuring means comprise a chamber 62 having an inlet 63 and an outlet 64 both connected to the circulation pipe 1 so that this chamber is traversed by the solution. These means also comprise a reference electrode 65 and a measuring electrode 66 being immersed in the solution via their extremities inside this chamber in a direction perpendicular to that of the circulation of the solution. These two electrodes are connected to a voltage measuring device 76, such as a millivoltmeter, having an output 3 constituting the output supplying the signal representative of the acidity of the solution. This signal is supplied to the computer 9. The electrodes 65, 66 have a cylindrical shape and are encompassed by an electrolyte (not shown on the figure) suitable for measuring the acidity of the solution in question. These electrodes are PHF100 type electrodes marketed by the TACUSSEL company.

For reasons to be explained later in detail, the installation also comprises at least one reference cell 67, diagrammatically shown as a longitudinal cutaway view on FIG. 4. Just like the circulation cell, this cell comprises a hollow cylinder 68 with several compartments; it is hermetically sealed and at its lower part contains a tank 69 identical to the transit tank. This tank is filled by a reference solution containing masses with known values of the metals in the solution. This reference cell makes it possible to calibrate the measurements and is introduced into the irradiation well 22 of FIG. 1 so as to carry out reference measurements. FIG. 4 also shows two pipes 70, 71, identical to the solution admission and evacuation pipes, which are used in the circulation cell. One of these pipes (for example, 70) is used to fill the tank 69 with the reference solution. These two pipes, the tank 69 and the entire lower part of the reference cell have dimensions and a structure identical to those of the circulation cell so as to avoid falsifying the reference measurements. After the tank 69 has been filled by the reference solution, the pipes 70, 71 are respectively hermetically sealed by stoppers 72, 73, whereas the upper part of the hollow cylinder 68 is hermetically sealed by a stopper 74.

In the embodiment where the installation is used for measurements concerning radioactive substances, the spectrometer 7, the irradiation well 22, the computer 9, as well as the printer 12 and memory 10 associated with said computer, the alarm triggering means 40 and the alarm (35 or 36) all collectively form a unit able to be moved close to the various glove boxes respectively corresponding to various solutions containing radioactive substances. In this case, each glove box includes its own flowmeters 4, acidity measurement means 2, a circulation cell 6, a stand-by receptacle 48 and a flexible sleeve 14. In fact, this moveable unit comprises the most costly devices of the installation. It is thus useful to be able to use it to carry out measurements of different solutions derived respectively from different glove boxes.

The installation described above functions as follows:

it is supposed that the solution, for example, is a nitric acid solution containing dissolved plutonium, uranium and americium. The keyboard of the computer 9 and the program contained in its memory 10 control the opening of the electrovalve 15 so as to ensure circulation of the solution in the pipe 1. This solution then circulates in the acidity measuring means 2, the flowmeter 4 and the circulation cell 6, the start up of the irradiation source 20 and the start of the measurement having been simultaneously controlled by the computer 9. During this circulation, the memory 10 of the computer periodically records the values of the acidity, flowrate and concentration of the various metals in the solution, these values being respectively provided by the acidity measurement means 2, the flowmeter 4 and the detector 21 of the spectrometer.

The measurement of the acidity of the solution makes it possible to correct the effect of the presence of nitric acid as regards the intensities of the energy peaks supplied by the detector 22 of the spectrometer. In fact, it is known that if the intensity of radiations derived from a solution with a thickness x is denoted by $I_2$, this solution being irradiated by radiations with an amplitude $I_1$, it is possible to write $I_2 = I_1 e^{-\mu x}$.

In this equation, $\mu$ denotes the absorption coefficient of the traversed material. In the example in question, this material contains nitric acid, as well as plutonium, uranium and americium nitrates.

In fact, the absorption coefficient $\mu$ is proportional to the sum of the nitric acid, plutonium, uranium and americium concentrations.

The nitric acid concentration is known by means of the acidity measurement means. The measurements of the intensities of the energy peaks supplied by the detector then make it possible to know the plutonium, uranium and americium concentrations. Knowing these concentrations and the flowrate of the solution makes it possible to deduce from these the masses of these various metals present in the solution.

The calculation of the concentrations is an iterative calculation making it possible to correct the values of the intensities of the energy peaks provided by the detector, these peaks often being accompanied by interference and trails falsifying the measurements. To this effect, the calculation program recorded in the memory 10 of the computer makes it possible, on the basis of the approximate values of the intensities of the energy peaks provided by the detector and from the approximating values of the intensities of the energy peaks of reference solutions measured from the reference cells mentioned above, to carry out iterative correction calculations making it possible to assess the best possible approximation of the real concentrations of the various metals in the solution.

What is claimed is:

1. Apparatus to carry out continuous measurements in real time of masses of metals in an acid solution and to measure the acidity of this solution, said apparatus comprising a circulation pipe for the circulation of a solution, means connected to the circulation pipe and traversed by the solution to measure the acidity of this solution, first output means operatively associated with said acidity measurement means for supplying a signal representative of the value of this acidity, a flowmeter operatively connected to the circulation pipe and traversed by the solution and operatively associated with second output means, said flowmeter providing on said second output means, a signal representative of the value of the flowrate of this solution, a cell for circulating the solution and operatively connected to the circulation pipe and traversed by the solution, a spectrometer operatively connected to the circulation cell and operatively associated with third output means, said spectrometer providing on said third output means, an intensity signal representative of the intensity of the energy peaks respectively corresponding to the values of the concentrations of metals in the solution, and computer means connected to said output means of the acidity measurement means, the spectrometer and the flow meter, said computer means also being connected to a memory in which a calculation program is recorded for calculating the respective masses of said metals from the values of said respective concentrations and from the values of the acidity and the flowrate, wherein said circulation cell comprises an admission pipe for admitting the solution into said cell, said admission pipe being operatively connected to said circulation pipe and a transit tank, and a pipe for evacuating the solution of said transit tank to a storage vessel, said spectrometer comprising a source for irradiating the solution, an energy peak detector having one output providing said intensity signal, and a sealed cylindrical irradiating well for receiving and irradiating said circulation cell at the time of measurements, said well being disposed vertically between the irradiation source and the detector so as to irradiate the solution in the transit tank, said well having a bottom and a cylindrical lateral wall and, at one upper extremity, an opening for introducing said cell into said well.

2. Apparatus according to claim 1, wherein said circulation cell is a sealed hollow cylinder containing said transit tank, said cylinder having an upper base traversed by said solution admission and evacuation pipes, a lower base with said transit tank being situated closer to said lower base than said upper base and a cylindrical casing integral with said bases, the introduction of said circulation cell into said irradiation well making a volume appear between said cylindrical casing of the cell and the inside of said well, this volume being hermetically sealed by joints for sealing the open space created between the circulation cell and the well.

3. Apparatus according to claim 2, further comprising means to detect any leak of the solution inside a detection volume, these detection means being connected to alarm triggering means, said detection volume being situated inside said cylinder between the lower base of said cylinder and the transit tank.

4. Apparatus according to claim 3, wherein the solution leak detection means include two electrodes located in the detection volume, these electrodes being connected to alarm triggering means by connecting means traversing the lower base of the circulation cell and the bottom of said irradiation well.

5. Apparatus according to claim 4, wherein an expansion volume for containing the solution in the event of any leak occurring is positioned above the transit tank inside said cylinder.

6. Apparatus according to claim 5, further comprising a circulation cell stand-by receptacle for supporting the circulation cell when no measurement is made, this receptacle being a cylindrical support vessel and having a bottom, one cylindrical lateral wall and an upper extremity having an opening for introducing the circulation cell, the introduction of the circulation cell into the support vessel making a volume appear between the cylindrical casing of the cell and the wall of the support vessel, this receptacle comprising means to detect any leaking of the solution in the volume between the casing of the cell and the wall of the support vessel, these means being connected to said alarm, the upper part of the cell comprising joints for maintaining a seal between the cell and the vessel.

7. Apparatus according to claim 6, wherein the flowmeter and the acidity measurement means are located in a glove box, said circulation pipe imperviously traversing this glove box, said solution admission and evacuation pipes traversing this glove box via a window having a circumference delimited by a frame, this frame being hermetically connected by a flexible sleeve to the upper base of the circulation cell, said admission and evacuation pipes being located in said sleeve, said evacuation pipe emptying into a vessel located inside the glove box, said stand-by receptacle being fixed in the glove box.

8. Apparatus according to claim 7, further comprising a plurality of glove boxes, wherein the spectrometer, the irradiation well, the computer, the alarm triggering means and the alarm collectively form a unit able to be moved close to said plurality of glove boxes glove boxes, each glove box in said plurality of glove boxes having its own flowmeter, acidity measurement means, circulation cell, stand-by receptacle and flexible sleeve.

9. Apparatus according to claim 7, wherein said calculation program is for calculating the respective values of said metals, which are plutonium, uranium and americium dissolved in nitric acid and the acidity of the solution of said metals.

10. Apparatus according to any of claims 1-7, wherein the acidity measurement means comprise a chamber having a solution inlet and a solution outlet both connected to said circulation pipe so that this chamber is traversed by the solution, a reference electrode and a measurement electrode immersed in the solution inside said chamber in a direction perpendicular to that of the solution circulation, these two electrodes being connected to a voltage measuring device having one output providing said signal representative of the acidity of the solution.

11. Apparatus according to any of claims 1-7, further comprising at least one reference cell including a hermetically sealed hollow cylinder containing a second tank identical to said transit tank, this second tank being filled by a reference solution containing masses of known values of the dissolved metals, this reference cell being introduced into the irradiation well so as to carry out measurements of the reference masses.

* * * * *